United States Patent
Shahrier et al.

(10) Patent No.: US 7,573,890 B2
(45) Date of Patent: Aug. 11, 2009

(54) METHOD AND SYSTEM FOR A LOW-OVERHEAD MOBILITY MANAGEMENT PROTOCOL IN THE INTERNET PROTOCOL LAYER

(75) Inventors: Sharif M. Shahrier, King of Prussia, PA (US); Prabhakar R. Chitrapu, Blue Bell, PA (US)

(73) Assignee: InterDigital Technolgy Corporation, Wilmington, DE (US)

( * ) Notice: Subject to any disclaimer, the term of this patent is extended or adjusted under 35 U.S.C. 154(b) by 6 days.

(21) Appl. No.: 11/542,842

(22) Filed: Oct. 4, 2006

(65) Prior Publication Data

US 2007/0025366 A1 Feb. 1, 2007

Related U.S. Application Data

(63) Continuation of application No. 10/078,946, filed on Feb. 20, 2002, now Pat. No. 7,136,389, which is a continuation-in-part of application No. 10/026,060, filed on Dec. 19, 2001, now abandoned, and a continuation-in-part of application No. 09/997,922, filed on Nov. 30, 2001, now abandoned.

(60) Provisional application No. 60/309,046, filed on Jul. 31, 2001, provisional application No. 60/296,168, filed on Jun. 6, 2001, provisional application No. 60/293,847, filed on May 25, 2001, provisional application No. 60/270,767, filed on Feb. 22, 2001, provisional application No. 60/270,190, filed on Feb. 21, 2001.

(51) Int. Cl.
*H04L 12/28* (2006.01)
*H04J 3/24* (2006.01)
*H04W 4/00* (2006.01)
*G06F 15/16* (2006.01)

(52) U.S. Cl. .................... 370/400; 370/331; 370/389; 370/475; 709/219

(58) Field of Classification Search ......... 370/312–331, 370/338–352, 389–395, 400–475; 709/203–219, 709/220–245; 455/430–435, 450–466
See application file for complete search history.

(56) References Cited

U.S. PATENT DOCUMENTS 6,058,431 A * 5/2000 Srisuresh et al. ............ 709/245

(Continued)

FOREIGN PATENT DOCUMENTS

EP 1009176 6/2000

(Continued)

OTHER PUBLICATIONS

"Special Issue on IMT-2000: Standardization Efforts of the ITU," IEEE Personal Communications Magazine; vol. 4, No. 4, pp. 8-40; (Aug. 1997).

(Continued)

*Primary Examiner*—Man Phan
(74) *Attorney, Agent, or Firm*—Volpe and Koenig, P.C.

(57) ABSTRACT

A system and method for supporting mobile Internet communication is provided which employs a plurality of Routers and a plurality of Mobile Nodes (MNs). Each Router has a unique communication address. Each MN is associated with a home Router. Each Router has an associated Mobile Node Location List identifying each MN for which the Router is the home Router and the communication address of a Router corresponding to a current location of each such MN. Each MN is movable from an old location where the MN communicates with the Internet via one Router to a current location where the MN communicates with the Internet via a different Router. Communication at the current location via the different Router is established by communicating to the MN's home Router the communication address of the different Router as the communication address corresponding to the MN's current location. Accordingly, a data communication from a corresponding node (CN) to a selected MN is communicated to the selected MN by accessing the Mobile Node Location List of the selected MN's home Router to determine the communication address corresponding to the selected MN's current location and directing the data communication to that determined communication address.

10 Claims, 4 Drawing Sheets

U.S. PATENT DOCUMENTS

| | | | |
|---|---|---|---|
| 6,115,580 A * | 9/2000 | Chuprun et al. | 455/1 |
| 6,240,514 B1 * | 5/2001 | Inoue et al. | 713/153 |
| 6,434,134 B1 | 8/2002 | La Porta et al. | |
| 6,452,920 B1 * | 9/2002 | Comstock | 370/349 |
| 6,487,406 B1 * | 11/2002 | Chang et al. | 455/422.1 |
| 6,496,505 B2 | 12/2002 | La Porta et al. | |
| 6,501,767 B1 | 12/2002 | Inoue et al. | |
| 6,510,153 B1 | 1/2003 | Inoue et al. | |
| 6,515,974 B1 * | 2/2003 | Inoue et al. | 370/331 |
| 6,535,493 B1 * | 3/2003 | Lee et al. | 370/329 |
| 6,577,643 B1 | 6/2003 | Rai et al. | |
| 6,587,882 B1 * | 7/2003 | Inoue et al. | 709/227 |
| 6,618,592 B1 * | 9/2003 | Vilander et al. | 455/452.1 |
| 6,621,810 B1 * | 9/2003 | Leung | 370/338 |
| 6,654,359 B1 | 11/2003 | La Porta et al. | |
| 6,856,624 B2 * | 2/2005 | Magret | 370/392 |
| 2001/0036184 A1 * | 11/2001 | Kinoshita et al. | 370/389 |
| 2002/0055971 A1 | 5/2002 | Shahrier | |
| 2002/0080752 A1 * | 6/2002 | Johansson et al. | 370/338 |

FOREIGN PATENT DOCUMENTS

| | | |
|---|---|---|
| EP | 1011241 | 2/2002 |
| JP | H 10-051449 | 2/1998 |
| JP | H10-051449 | 2/1998 |
| JP | 11-353360 | 12/1999 |
| JP | 2000-092562 | 3/2000 |
| JP | 2000-149104 | 5/2000 |
| KR | 2000-0077204 | 12/2000 |

OTHER PUBLICATIONS

Blake et al., "An Architecture for Differentiated Services," RFC 2475, (Dec. 1998).
Bradner, "Key Words for Use in RFCs to Indicate Requirement Levels," BCP 14, RFC 2119, (Mar. 1997).
Campbell et al., "Cellular IP," Internet Draft, (Oct. 1999).
Jain et al., "Mobile Internet Access and QoS Guarantees Using Mobile IP and RSVP with Location Registers," 1998 IEEE International Conference on Communications, 1998. ICC 98. Conference Record., vol. 3, pp. 1690-1695 (Jun. 7-11, 1998).
Kempf, "Problem Description: Reasons for Performing Context Transfers between Nodes in an IP Access Network," Internet Draft, (May 2002).
Levkowetz et al., "Problem Description: Reasons for Doing Context Transfers Between Nodes in an IP Access Network," Internet Draft, (Jan. 2001).
Perkins, "IP Mobility Support," RFC 2002, (Oct. 1996).
Ramjee et al., "IP Micro-Mobility Support Using Hawaii," Internet Draft, (Jul. 2002).
Shelby et al., "Cellular IPv6," Internet Draft, (Jul. 2001).
Xu et al., "Mobile IP Based Micro Mobility Management Protocol in the Third Generation Wireless Network," Internet Draft, (Nov. 2000).

*Bradner; "Key Words for Use in RFCs to Indicate Requirement Levels;" BCP 14, RFC 2119; Mar. 1997.
*Special Issue on IMT-2000: Standardization Efforts of the ITU, IEEE Personal Communications Magazine; vol. 4, No. 4, pp. 8-40; Aug. 1997.
*Perkins, IP Mobility Support, RFC 2002, Oct. 1996.
*Campbell et al., Cellular IP, Internet Draft, Oct. 1999.
*Ramjee et al., IP Micro-Mobility Support Using Hawaii, Internet Draft, Jul. 2002.
*Xu et al., Mobile IP Based Micro Mobility Management Protocol in the Third Generation Wireless Network, Internet Draft, Nov. 2000.
*Levkowetz et al., Problem Description: Reasons for Doing Context Transfers Between Nodes in an IP Access Network, Internet Draft, Jan. 2001.
*Blake, et al., An Architecture for Differentiated Services, RFC 2475, Dec. 1998.
Yokota et al., "A Study on Applying Mobile IP to Mobile Backbone Network," IPSJ SIG Notes, vol. 2000, No. 87, Information Processing Society of Japan, pp. 69-76 (Sep. 22, 2000).
"Special Issue on Imt-2000: Standardization Efforts of the Itu," IEEE Personal Communications Magazine; vol. 4, No. 4, pp. 8-40; (Aug. 1997)..
Bhag What et al., "Network Layer Mobility: an Architecture and Survey," IEEE Personal Communications, pp. 54-64 (Jun. 1996).
Blake et al., "An Architecture for Differentiated Services," RFC 2475, (Dec. 1998).
Bradner, "Key Words for Use in RFCs to Indicate Requirement Levels," BCP 14, RFC 2119, (Mar. 1997).
Jain et al., "Mobile Internet Access and QoS Guarantees Using Mobile IP and RSVP with Location Registers," 1998 IEEE International Conference on Communications, 1998. ICC 98. Conference Record., vol. 3, pp. 1690-1695 (Jun. 7-11, 1998).
Kempf, "Problem Description: Reasons for Performing Context Transfers between Nodes in an IP Access Network," Internet Draft, (May 2002)..
Levkowetz et al., "Problem Description: Reasons for Doing Context Transfers Between Nodes in an IP Access Network," Internet Draft, (Jan. 2001)..
Ramjee et al., "IP Micro-Mobility Support Using Hawaii," Internet Draft, (Jul. 2002).
Xu et al., "Mobile IP Based Micro Mobility Management Protocol in the Third Generation Wireless Network," Internet Draft, (Nov. 2000).
Yokota et al., "A Study on Applying Mobile IP to Mobile Backbone Network," IPSJ SIG Notes, vol. 2000, No. 87, Information Processing Society of Japan, pp. 69-76 (Sep. 22, 2000)..

* cited by examiner

| CN binding to MN | |
|---|---|
| Global Address of CN's NAT | Local Address of CN in NAT |
| Global Address of MN's NAT | Local Address of MN in NAT |

48 bits

|1| | | | | | | | | | | | | | | | | | | | | | |24|25| | | | | | | | | | | | | | | | | | | | | | |48|

Figure 7
(Prior Art)

| Mobile-Home Database (NAT-B) | | | |
|---|---|---|---|
| Mobile Node (HA or VA) | Flag | Local Address (COA) | NAT Address |
| $MN_{0,B0}$ @ $Host_{B0}$ | 0 | $MN_{0,B0}$ @ $Host_{B0}$ | null |
| $MN_{1,B0}$ @ $Host_{B0}$ | 0 | $MN_{1,B0}$ @ $Host_{B1}$ | null |
| $MN_{0,B1}$ @ $Host_{B1}$ | 0 | $MN_{0,B1}$ @ $Host_{B1}$ | null |
| ... | ... | ... | ... |
| $MN_{i,Nk}$ @ $Host_{B1}$ | 0 | $MN_{i,Nk}$ @ $Host_{B1}$ | null |
| $MN_{h,Pq}$ @ $Host_{B1}$ | 0 | null | null |
| ... | ... | ... | ... |

Figure 8

| Mobile-Home Database (NAT-N) | | | |
|---|---|---|---|
| Mobile Node (HA or VA) | Flag | Local Address (COA) | NAT Address |
| ... | ... | ... | ... |
| $MN_{m,Nj}$ @ $Host_{Nj}$ | 0 | $MN_{m,Nj}$ @ $Host_{Nk}$ | null |
| ... | ... | ... | ... |
| $MN_{0,Nk}$ @ $Host_{Nk}$ | 0 | $MN_{0,Nk}$ @ $Host_{Nk}$ | null |
| ... | ... | ... | ... |
| $MN_{i,Nk}$ @ $Host_{Nk}$ | 1 | $MN_{i,Nk}$ @ $Host_{B1}$ | NAT-B |
| ... | ... | ... | ... |

Figure 9

METHOD AND SYSTEM FOR A LOW-OVERHEAD MOBILITY MANAGEMENT PROTOCOL IN THE INTERNET PROTOCOL LAYER

CROSS-REFERENCE TO RELATED APPLICATIONS

This application is a continuation of U.S. patent application Ser. No. 10/078,946, filed Feb. 20, 2002, now U.S. Pat. No. 7,136,389, which is a continuation-in-part of U.S. patent application Ser. No. 09/997,922, filed Nov. 30, 2001 now abandoned and U.S. patent application Ser. No. 10/026,060, filed Dec. 19, 2001, now abandoned which in turn claim priority from U.S. Provisional Patent Application Ser. No. 60/309,046, filed Jul. 31, 2001; U.S. Provisional Patent Application Ser. No. 60/296,168, filed Jun. 6, 2001; U.S. Provisional Patent Application Ser. No. 60/293,847, filed May 25, 2001; U.S. Provisional Patent Application Ser. No. 60/270,767, filed Feb. 22, 2001; and U.S. Provisional Patent Application Ser. No. 60/270,190, filed Feb. 21, 2001 which are all incorporated by reference herein.

FIELD OF THE INVENTION

The present invention relates to a system and method of mobile Internet communication capable of a high rate of data transmission which also supports many types of traffic flows, including both real-time and non real-time services. Specifically the present invention relates to a method of managing the mobility of a Mobile Node (MN) within multiple administrative domains. In one embodiment, the multiple administrative domains employ Network Address Translation enabled routers (NATs) for Internet communications.

BACKGROUND OF THE INVENTION

In a mobile network, each Mobile Node (MN) is in communication with a single Access Point (AP) and receives communication via an Access Router (AR) associated with the AP. This situation represents a single point of attachment of the MN to the Internet. Conventionally, mobility management schemes use a two-level hierarchical approach to mobile Internet Protocols (IPs). Where a MN had moved from its home AP, the home AR receives and repackages a communication in a datagram from a source node, commonly called a Corresponding Node (CN), by adding a new header to a received datagram to redirect and "tunnel" the CN communication to the current IP address of the MN. The new/repackaged datagram encapsulates the original CN datagram in its data portion which is commonly referred to as internet protocol-in-internet protocol (IP-in-IP) encapsulation.

Network Address Translation enabled routers (NATs) may be used for connecting private networks to the Internet. As illustrated in FIG. 7, conventional Internet communications are conducted by establishing 48 bit bindings between NATs which identify nodes which are communicating with each other. The address space is divided into a set of registered 24 bit global addresses and a set of unregistered 24 bit local addresses by the Internet Address Numbers Authority (IANA). Private networks can use any address from the unregistered address space. The public or global addresses are registered and one address from this pool is assigned to each NAT.

The inventor has recognized that it would be desirable to modify the traditional Network Address Translation functions to handle the cases where Mobile Nodes (MNs) are allowed to migrate within their own private networks and where MNs are allowed to migrate from one private network to another.

SUMMARY

The present invention is directed to a novel system and method that combines mobility management with optimal routing for use over a mobile air interface.

A network system for supporting mobile Internet communication comprises a plurality of Routers and a plurality of Mobile Nodes (MNs) is provided. Each Router has a unique communication address. Each MN is movable to various locations to communicate with the Internet via different Routers at different locations. Each MN is associated with a home Router.

Each Router has an associated Mobile Node Location List identifying each MN for which the Router is the home Router and the communication address of a Router corresponding to a current location of each such MN. Each MN is movable from an old location where the MN communicates with the Internet via one Router to a current location where the MN communicates with the Internet via a different Router. Communication at the current location via the different Router is established by communicating to the MN's home Router the communication address of the different Router as the communication address corresponding to the MN's current location. Accordingly, a data communication from a corresponding node (CN) to a selected MN is communicated to the selected MN by accessing the Mobile Node Location List of the selected MN's home Router to determine the communication address corresponding to the selected MN's current location and directing the data communication to that determined communication address.

In one embodiment, the network includes a plurality of Access Routers (ARs) as the Routers. Each AR has a unique Internet Protocol (IP) address and a geographic access range in which the ARs communicate data to the MNs. Each MN is associated with a home AR and each AR has as its Mobile Node Location List an associated Node Location Table (NLT). The NLT identifies each MN for which the AR is the home AR and the IP address of a current location of each such MN.

Each MN is movable outside the access range of its home AR to a location within the access range of a selected one of any of the other ARs to receive data via the selected AR. To do so, the MN communicates to its home AR the IP address of the selected AR as its current location. Thus, a data communication from another node, commonly referred to as a corresponding node (CN), to a selected MN is communicated to the selected MN by directing a query to the IP address of the selected MN's home AR, receiving the IP address of the current location of the selected MN from the NLT of the selected MN's home AR and directing the data communication to the received IP address.

Preferably, the network system includes a plurality of Access Points (APs). At least one AP is associated with each AR such that the MNs communicate with the ARs via the APs. Each AP has an access range in which the AP communicates data to MNs. The access ranges of the APs associated with a given AR collectively define the access range of that AR.

Preferably the network system also includes a plurality of Access Network Gateways (ANGs). At least one AR is associated with each ANG and each ANG is coupled with the Internet.

A novel method of communication between a Corresponding Node (CN) and a Mobile Node (MN) over the Internet using standard format datagrams is provided. In general the standard format for Internet datagrams are datagrams which have a header portion and a data portion where the header portion includes a source Internet Protocol (IP) address, a destination IP address and a protocol type. In the inventive method, the CN communicates with the Internet via an AR having a first IP address, the MN is associated with a home AR having a second IP address and the MN is in communication with the Internet via an AR having a third IP address. The second and third addresses are the same where the MN is communicating via its home AR.

The CN sends a first datagram identifying the first IP address as the header source IP address, the second IP address as the header destination address, an Internet Control Message Protocol (ICMP) as the header protocol type, and a query as to the location of the MN is included in the data portion of the first datagram. The home AR receives the first datagram from the CN and replies with a second datagram wherein the second IP address is the header source IP address, the first IP address is the header destination IP address, an ICMP is the header protocol type, and a query reply containing the third IP address is included in the data portion of the second datagram. The CN receives the second datagram and sends at least a third datagram having the first IP address as the header source IP address, the third IP address as the header destination IP address, a data message protocol as the header protocol type and includes an identification of the MN and communication data for the MN in the data portion of the third datagram. The MN receives the communication data contained in the third datagram via the AR with which the MN is in communication.

Preferably, the home AR maintains a Node Location Table (NLT) identifying each MN for which the AR is the home AR and the IP address of a current location of each such MN. The home AR, accordingly, creates the data portion of the second datagram by referencing the Node Location Table (NLT).

The method also preferably includes the MN sending a standard format datagram when the MN communicates with the Internet via an AR which is not its home AR. The MN datagram includes the third IP address as the header source IP address, the second IP address as the header destination IP address, a User Data Protocol (UDP) as the header protocol and includes an identification of the home AR and the third IP address in the data portion of the MN datagram. The home AR receives the MN datagram and uses the data portion thereof to update the NLT associated with the home AR.

In another embodiment, each Router is a Network Address Translation router (NAT). The system then preferably comprises a plurality of networks where each network has a different one of the NATs with a unique global address, at least one Host associated with the NAT and at least one Mobile Node (MN). The Mobile Nodes (MNs) communicate within the system via the Hosts.

Each Host is associated with one NAT and has a service area in which it can communicate data to the MNs. Each MN has a home Host within a home network which defines a default local address which is paired with the global address of the home network's NAT to define a default binding of the MN.

The invention provides the NAT of each network with an associated Mobile-Home Database (MHD) as its Mobile Node Location List which identifies each MN, which has the network as its home network, with a) a local address of a current association of the MN with a Host within the network or b) a binding defined by a local address of an association of the MN with a Host within a different network and the global address of the different network's NAT. Each network's NAT's MHD also identifies each visiting MN, i.e. an MN which is currently associated with a Host associated with the NAT, but has a different home network, with a local address of the current Host association of the MN.

Each MN can be moved from a location where the MN communicates data via a first associated Host within a first network having a first NAT to a location within the service area of a second Host within the first network to communicate data via the second Host. MN communication via the second host is enabled by communicating to the MHD of the first NAT a local address reflecting the MN's association with the second Host.

Each MN can also be moved from a location where the MN communicates data via the first associated Host within the first network to a location within the access range of a third Host within a different second network having a second NAT to communicate data via the third Host. MN communication via the third Host is enabled by communicating to the MHD of the second NAT a local address reflecting the MN's association with the third Host. Where the second network is not the MN's home network, the MN also communicates to the MHD of the MN's home network's NAT a binding including a new local address reflecting the MN's association with the third Host and the global address of the second NAT.

The system enables a data communication from a corresponding node (CN) to a selected MN to be communicated to the selected MN by establishing a binding based on the MN's default binding or the binding reflected in the MHD of the MN's home network's NAT. The NAT with which the binding is established directs the communication to the local address identified in its MHD for the MN.

A preferred system includes at least one network associated with a plurality of Hosts and at least one Host which is the home Host for a plurality of MNs. Nodes that are not mobile may also be associated with the Hosts within the system. These nodes can be configured to bypass the MHD for communications directed to non-mobile nodes Preferably, the NAT's MHD of each network identifies 24 bit local and global addresses and a location field. Each MN, which has the network as its home network, is identified in the NAT's MHD with a) a local address of a current association of the MN with a Host within the network, a null global address, and a home flag in the location field or b) a binding defined by a local address of an association of the MN with a Host in a different network and a global address of the different network's NAT and an away flag in the location field. Each visiting MN is preferably identified in the visited network's NAT's MHD with a local address of the current Host association of the MN, a null global address, and a home flag in the location field. A binding is established between a source/corresponding node (CN) and an MN based on the binding reflected in the MHD of the MN's home network's NAT when the corresponding location field has an away flag.

The present invention can be used to implement an Internet architecture consisting of a large number of private networks, individually connected to the Internet backbone via NATs. Hosts within the same private network can communicate with one another, and also with external Hosts via the Internet backbone. The routers in each private network maintain their own local routes and routers in the backbone maintain their own external routes. More specifically, the routers within a particular domain are not cognizant of routes outside that domain. Likewise, the backbone (public) routers are not cognizant of the routes to any local addresses.

BRIEF DESCRIPTION OF THE DRAWING(S)

FIG. 7 is a diagram of a conventional Internet communication binding;

Figure 6:
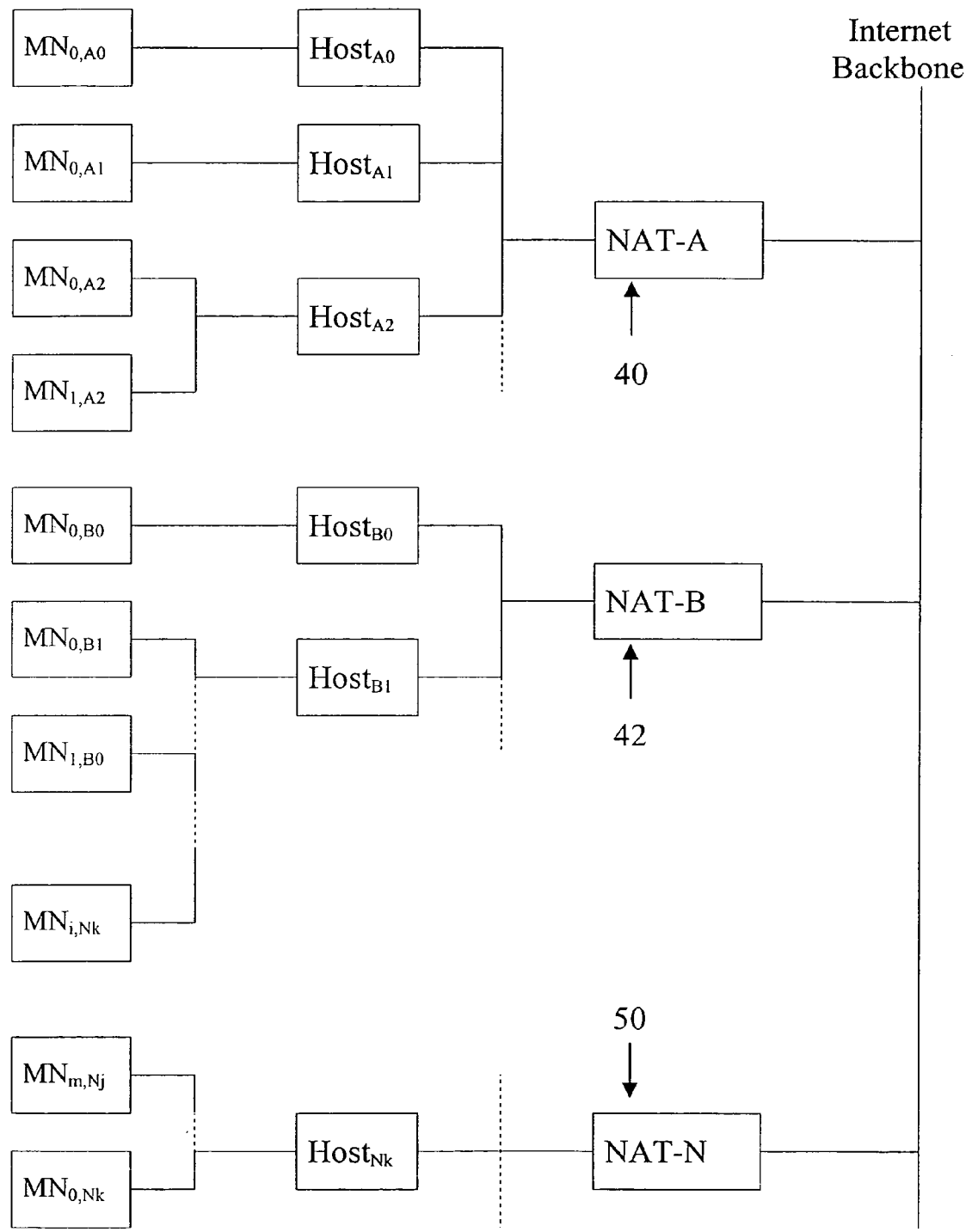
FIG. 6 is a schematic diagram of an architecture and topology of a mobile network associated with the Internet as applicable to a second embodiment of the invention.

FIG. 8 illustrates a portion of a Mobile-Home Database (MHD) of one of the Network Address Translation Routers (NATs) illustrated in FIG. 6 in accordance with the teachings of the present invention; and FIG. 9 illustrates a portion of a Mobile-Home Database (MHD) of one of the Network Address Translation Routers (NATs) illustrated in FIG. 6 in accordance with the teachings of the present invention.

TABLE OF ACRONYMS

The following acronyms are used herein:
ANG Access Network Gateway
AP Access Point
AR Access Router
BER Bit-Error Rate
CN Corresponding Node
COA Care of Address
DNS Domain Name Server
FN Foreign Network
HA Home Address
HNI Home Network Identifier
IANA Internet Address Numbers Authority
ICMP Internet Control Message Protocol
IETF Internet Engineering Task Forces
IP Internet Protocol
IP in IP Internet Protocol-In-Internet-Protocol
MCN Mobile Communication Network
MHD Mobile-Home Database
MN Mobile Node
NAT Network Address Translation Router
NDP Neighborhood Discovery Protocol
NLT Node Location Table
OSPF Open Shortest Path First
QoS Quality of Service
TCP/IP Transmission Control Protocol/Internet Protocol
UDP User Datagram Protocol
VA Visiting Address
3GPP Third Generation Partnership Project

DETAILED DESCRIPTION OF THE PREFERRED EMBODIMENT(S)

The present invention provides improvements over existing mobility management protocols, in particular, current 3GPP Mobile IP. The present invention eliminates the need for IP-in-IP encapsulation from a CN to a MN while including the identity of the original CN in the IP datagram, optimizes routing from sender to receiver, using OSPF, i.e. no need to tunnel via the home AR as in Mobile IP. Although this invention is applicable to both wireless and wireline networks, the reduction of overhead make the invention particularly useful for wireless over the air interface communication in 3GPP Mobile IP networks.

Figures 1, 2:
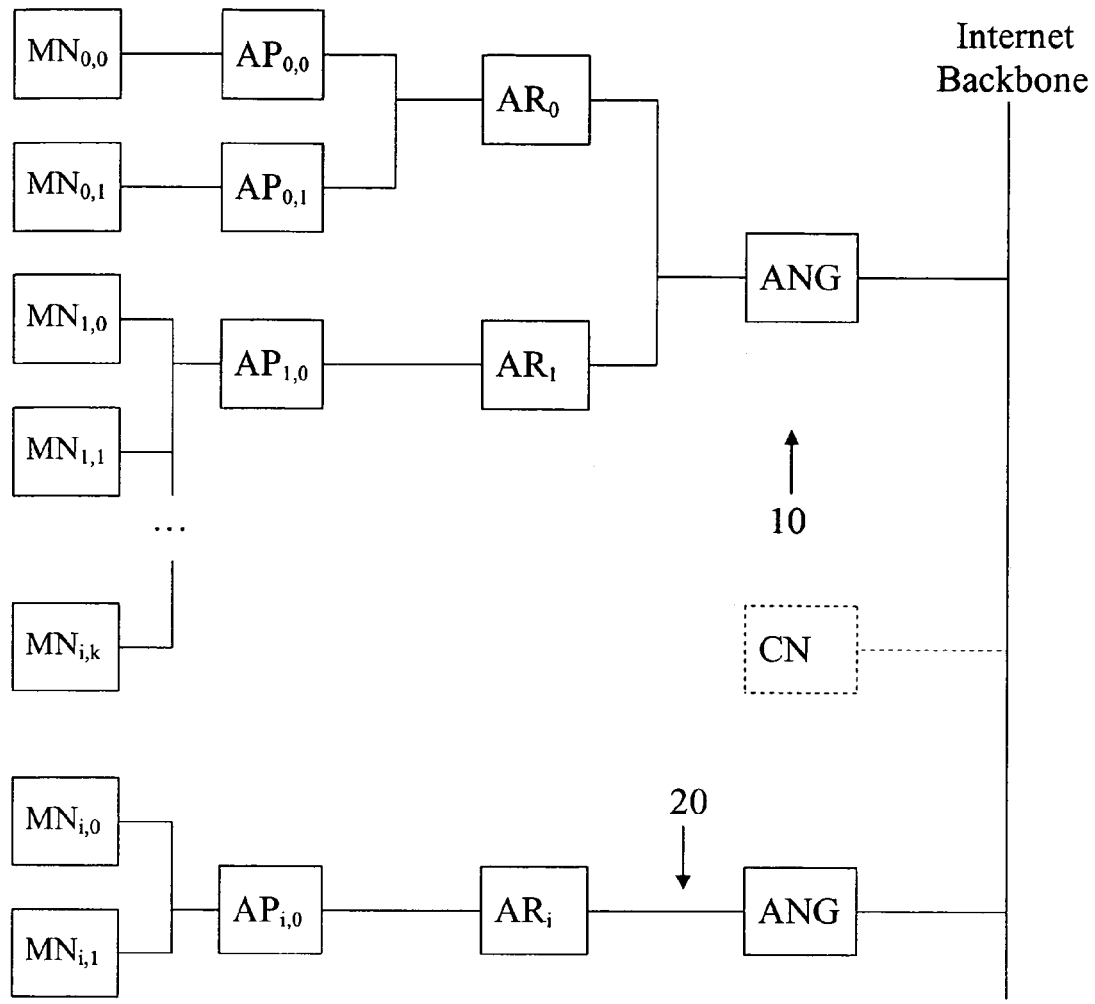
FIG. 1 is a schematic diagram of an architecture and topology of a mobile network associated with the Internet.
FIG. 2 illustrates a Node Location Table for an Access Router in accordance with the teachings of the present invention.

Referring to FIG. 1, there is shown the architecture and topology of a typical mobile communication network (MCN). The illustrated elements are associated with the following terminology and definitions. Mobile Node (MN) means an IP mobile terminal capable of changing its point of attachment to the internet. Access Point (AP) is an access point offering a wired or wireless air-interface connection to the MNs. The invention as applied to facilitating hand-off of a continuous communication would typically only be used in connection with wireless MN interfaces. Access Router (AR) is an IP router connected to one or more APs. Each AR represents a single IP address. Access Network Gateway (ANG) is an IP gateway that connects the sub-networks to the Internet backbone. A combination of ARs connected to the same ANG belong to the same sub-network. Conversely, ARs connected to different ANGs are part of different sub-networks.

Each MN is pre-designated to a single sub-network called its "home network". Each home network is identified by an identifier called the Home Network Identifier (HNI). Within its home network, the MN is connected to an access point called a "home AP", which in turn is connected to a router called a "home AR". Every AR has a unique IP address, so that the link between a MN and its home AR represents a single connection point to the Internet. Every MN in the network is assigned a fixed value called its host-name which is also commonly called its node name. The MN host-name does not change as the MN moves around the MCN. In particular, whenever any MN connected to the AR queries an Internet Domain Network Server (DNS) with a <HNI,host-name> pair of a specific MN, the DNS returns with the IP address of the home AR of the specific MN.

It is well known to send TCP/IP (Transmission Control Protocol/Internet Protocol) data packets to accomplish the transmission of data from a source node to a target node. A Destination IP Address in the IP header is used to route the packet to the target AR. The AR then broadcasts the data packet to all the AP's attached to it. The TCP "destination port number" field contains the host-name of the target MN. Each AP registers the host-names of the MNs that are currently attached to it. If an AP receives a packet whose port number (host-name) matches one of its registered host-names, the packet is transmitted through the interface to that MN. Otherwise the packet is discarded.

FIG. 1 schematically illustrates two sub-networks 10, 20 which each communicate with the Internet via its own ANG. The first sub-network 10 includes ARs, $AR_0$ and $AR_1$. The router $AR_0$ is associated with Access Points $AP_{0,0}$ and $AP_{0,1}$. A Mobile Node $MN_{0,0}$ is associated with $AP_{0,0}$ as its home AP and $AR_0$ as its home AR. A Mobile Node $MN_{0,1}$, is associated with $AP_{0,1}$ as its home AP and $AR_0$ as its home AR. The second Access Router $AR_1$ of the sub-network 10 is associated with Access Point $AP_{1,0}$. Mobile nodes $MN_{1,0}$ and $MN_{1,1}$ have $AP_{1,0}$ as their home AP and $AR_1$ as their home AR.

The second sub-network 20 includes Access Router $AR_i$ and associated Access Point $AP_{i,0}$. Mobile nodes $MN_{i,0}$ through $MN_{i,k}$ are associated with Access Point $AP_{i,0}$ as their home AP and Access Router $AR_i$ as their home AR. Only mobile nodes $MN_{i,0}$, $MN_{i,1}$ and $MN_{i,k}$ are illustrated for simplicity. Mobile node $MN_{i,k}$ is illustrated as in communication with the Internet via the first sub-network 10 through Access Point $AR_{1,0}$ and Access Router $AR_1$.

The mobility management protocol of the present invention is designed for mobile nodes migrating around a Mobile Core Network. This protocol is suitable for MNs moving within a single sub-network or across multiple sub-networks. According to the protocol of the present invention the source is advised of the target's new location, every time the target moves to a new AR. If the MN moves to a new AP, but it is still attached to the same AR, it means that the IP address associated with the MN has not changed. Conversely, if a MN becomes attached to a different AR, the IP address is changed to indicate a new route. For example, mobile node $MN_{i,k}$ is illustrated as being away from its home sub-network 20 and is in communication with the Internet via the address of router $AR_1$, not the address of router $AR_i$.

Mobile Node $MN_{0,0}$ of FIG. 1, could potentially relocate to communicate through access point $AP_{0,1}$ instead of its home access point $AP_{0,0}$. In that case, $MN_{0,0}$ would remain in communication with the Internet via its home Access Router $AR_0$ so that its associated IP address would not have changed. However, if mobile node $MN_{0,0}$ accesses the Internet via Access Point $AP_{1,0}$, its IP address will change to the address of Access Router $AR_1$, even though $MN_{0,0}$ remains within its home sub-network 10.

During the normal course of operation, MNs may move throughout the MCN. To facilitate the ability to locate an MN at any given time, each AR maintains a directory, called a "Node Location Table" (NLT). The NLT contains a listing of the node names (host-names) of all the MNs for which the AR is a home AR, and their current locations as reflected by the IP address of the AR with which the MN is in communication with the Internet. If the MN is at its home AR, then the IP address is that of its home AR. However, if the MN has moved away from its home AR, then the IP address is that of a foreign AR.

FIG. 2 illustrates a Node Location Table 30 associated with access router $AR_i$ of the sub-network 20 with entries for the MNs as depicted in FIG. 1. The current location of the Mobile Nodes which are "home" is the IP address of $AR_i$. The Table 30 reflects that the current IP address for $MN_{i,k}$ is the IP address of router $AR_1$ of sub-network 10 which is in conformance with the illustrated location of $MN_{i,k}$.

Before IP datagrams can be sent to a target MN, a TCP connection has to be established between the AR of the source or corresponding node (CN) and the AR of the target MN. Before such an event, the source CN ascertains the target mobile's current location. This is accomplished by exchanging a pair of ICMP (Internet Control Message Protocol) messages using standard format datagrams between the peers. ICMP is a well known protocol used within the data portion of standard format Internet datagrams. ICMPs have a TYPE field of which types 20 and 21 are heretofore not used.

Figure 3:
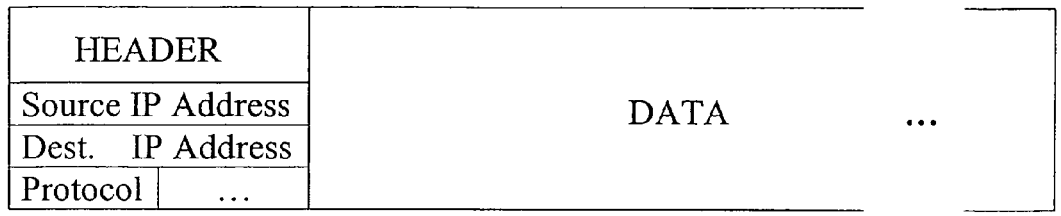
FIG. 3 is a diagram of a conventional Internet datagram.

FIG. 3 illustrates a standard format datagram for Internet communications. The datagram includes a header portion and a data portion. The header portion includes a source IP address field, a destination IP address field, and a protocol type field. The data portion corresponds to the type of protocol indicated in the header protocol type field.

Figure 4:
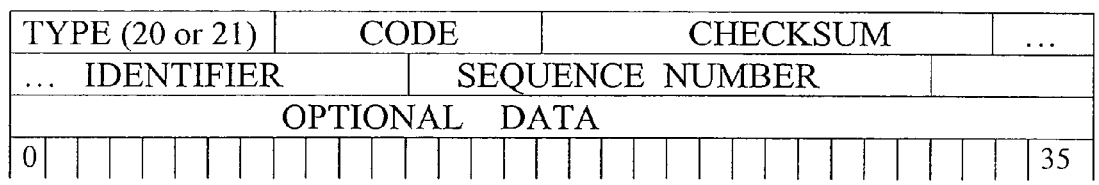
FIG. 4 is a diagram illustrating an Internet Control Message Protocol (ICMP) format in accordance with the teachings of the present invention.

FIG. 4 illustrates a format of an ICMP which is communicated in the data portion of a standard format Internet datagram. The ICMP of FIG. 4 includes a type field, a code field, a checksum field, an identifier field, a sequence number field, and an optional data field in accordance with conventional ICMP format. The ICMPs of the present invention preferably use type 20 or 21 in the type field as explained in more detail below, but could use any previously undefined type for the purposes of this invention.

To communicate data from a CN to an MN, the CN first indexes into a DNS using the node-name of the target MN and retrieves the MN's home IP address in accordance with conventional protocol. Next, the CN constructs a standard format datagram containing a header portion and an ICMP node location query message in a data portion. The CN datagram header contains the IP address of the CN's AR as the header source IP address, the MN's home AR IP address as the header destination address, and '1', which currently is assigned for ICMPs as the header protocol type. The ICMP node location query message is provided with the following field settings:

TYPE=20—Node location query.
IDENTIFIER=node-name—Node-name of target MN.

The rest of the fields are filled in a conventional manner and the resulting ICMP message is placed in the data portion of the CN IP datagram frame. The resulting IP datagram is sent to the target MN's home AR. When received, the target MN's home AR evaluates the checksum data to ascertain proper reception of the ICMP query message from the CN. If the checksum does not indicate a proper ICMP message no response is made and the CN must resend its query. If the ICMP message is properly received, the target MN's home AR uses the CN's ICMP's Identifier to index into the NLT and retrieve target MN's current IP address. The target MN's home AR then constructs a responsive datagram having a reply ICMP message and sends it back to the CN. The responsive datagram's header contains the target MN's home AR IP address as the header source IP address, the IP address of the CN's AR as the header destination address, and '1', which currently is assigned for ICMPs, as the header protocol type. The ICMP node location query reply message is provided with the following field settings:

TYPE=21—Node location query reply.
IDENTIFIER=Node-name of CN.
OPTIONAL DATA=Target MN's current IP address.
CODE=1 or 13—'1' indicating that the MN is unavailable and '13' indicating that the MN is available.

The rest of the fields are filled in a conventional manner and the resulting ICMP message is placed in the data portion of the responsive datagram frame. Optionally, the MN's home AR can send a message to the target MN at the IP location indicated in the NLT to determine if the MN is actively connected to the Internet. If no acknowledgment of that inquiry is received in a selected time out period, the MN's home AR would use CODE '1' in the reply to the CN. In that case the AR could also be configured to reset the current location of the target MN to the home AR in the NLT.

The resulting IP datagram is sent to the CN. When received, the CN's AR evaluates the checksum data to ascertain proper reception of the ICMP query reply message. If the checksum does not indicate a proper ICMP message no action is taken and the CN must resend its query since it will not receive the reply. If the ICMP message is properly received, the CN's AR uses the ICMP's Identifier to forward the target MN's current IP address to the CN and the information as to whether the CN is available.

Once the IP address is known, a TCP connection is established between the sender CN and receiver MN and the data transfer takes place. Assuming the MN is available, the CN constructs one or more TCP/IP datagrams having the data for the target MN and sends it directly to the MN at its current IP address. The TCP/IP datagrams headers contain the IP address of the CN's AR as the header source IP address, the target MN's current AR IP address as the header destination address, and '6', which currently is assigned for TCP/IP data, as the header protocol type.

If a target MN relocates to a new AP while it is still communicating with the CN, 'hand off' is performed. For hand off, the CN is notified of the new location of the target MN, so that the target MN can continue to receive data seamlessly. If, after relocation, the new AP of the target MN is connected to the same AR, i.e. the MN's current IP address remains the same and the connection can continue to proceed as normal. If, on the other hand, the MN moves to an AP with a different AR, the MN's current IP address changes and the CN needs to be notified of the new IP address. Once notified, the CN uses the new current IP address of the target MN as the header destination address in the TCP/IP datagrams.

Figure 5:
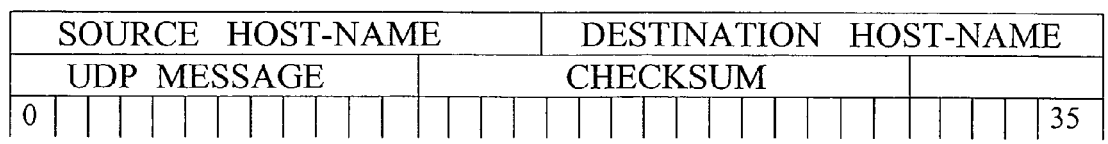
FIG. 5 is a diagram illustrating a User Data Protocol (UPD) messaging format in accordance with the teachings of the present invention.

To re-direct the data traffic flow, the MN sends a User Data Protocol (UDP) message to both the CN and the MN's home AR containing the new current IP address of the target MN. Where an ongoing communication is not being conducted with a CN, a UDP message datagram is only sent to the MN's home AR. This also occurs upon MN reconnection, if the MN disconnects from the Internet altogether by being relocated to a position outside the access range of all compatible APs or by simply being turned off. FIG. 5 illustrates the format of a UDP message used in accordance with the teachings of the present invention.

The UDP message includes a source host-name field, a destination host-name field, a UDP message field and a checksum field. In the MN's UDP message, the node name of the MN is placed in the source host-name field and the CD's node name or MN's home AR's node name, respectively, is placed in the destination host-name field. The new MN current IP address is placed in the UDP message field of the UDP message. The UDP message length is normally set to 12 bytes because it is 3 words long.

The UDP message is included as the data portion of a standard format datagram as illustrated in FIG. 3. The target MN's datagram header contains the IP address of the CN's AR or the MN's home AR's IP address as the header destination IP address, respectively, and the protocol type is indicated as "17", which is currently the identification assigned for UDP messages.

The header source IP address of the MN's UDP message datagram will either be the "old" MN current IP address or the "new" MN current IP address dependent upon the type of hand over which is being implemented. A preferred method of implementing hand over is "make before break" in which the MN obtains the address of the new AR with which it will communicate before ceasing communication via the existing ("old") AR. In such instances, the MN's datagram header source IP address will be the existing ("old") IP address with the MN's new location IP address being stored in the UDP message field of the UDP message within the MN's datagram. Otherwise, the UDP message is communicated after communication has commenced with the target MN via the new AR and the MN's UDP message datagram will have the address of the new AR as the header source IP address.

In order for the target MN to obtain the address of the new AR with which it will communicate, the MN sends a conventional Neighborhood Discovery Protocol (NDP) message. The NDP message is a standard protocol which returns the IP address of the router associated with the AP which has an access range into which the target MN has relocated. The MN then sends the UDP message datagrams to advise the CN and the MN's home AR of the NDP results. The home AR updates its NLT with the new IP address received in the MN's UDP message datagram.

Optionally, the home AR can send an acknowledgment UDP message or other type of acknowledgment message to the MN to confirm the updating of the NLT. This is important to handle the case where the check sum of the UDP received by the MN's home AR is bad. In such case, the NLT will not be updated since the home AR will not process the information in the UDP. Acknowledgment by the home AR to the MN permits the MN to resend the UDP message, in the absence of an acknowledgment, within a selected time-out period.

In the case where the target MN moves while receiving data from a CN, the MN sends the UDP message containing the results of the NDP to the CN. The CN then redirects the TCP/IP datagrams by using the new AR IP address as the header destination IP address in the TCP/IP datagrams. For data blocks being transmitted in the transitional period, the MN and CN can communicate to determine the last successfully received TCP/IP datagram by the target MN from the CN so that the CN can resend any missing TCP/IP datagrams to the target MN at the new IP address. Alternatively, provisions can be made to forward datagrams which are not received by the target MN from the "old" AR to the "new" AR.

As illustrated in FIG. 6, a second embodiment of the invention is implemented where private networks 10, 12, 20 are connected to an external Internet backbone via Network Address Translation enabled routers (NATs). Using such a scheme, large number of private networks can be connected to the external Internet backbone. Hosts within different private networks can communicate with each other via the backbone, using the NAT registered addresses assigned by IANA. Hosts within the same private network can communicate with each other using one of the unregistered addresses. Thus, the registered addresses are globally unique, while unregistered addresses have local significance only. The local addresses and the global addresses are mutually exclusive and are conventionally 24 bits each.

For example, networks 40, 42 and 50 are connected to the Internet via NAT enabled routers NAT-A, NAT-B and NAT-N, respectively. NAT-A, NAT-B and NAT-N are each assigned a unique Global Address by IANA. Nodes within each private network 40, 42, 50 are assigned local address based upon the Host to which the node is connected. For example, node $MN_{0,40}$ is illustrated as connected to the private network 10 via $Host_{40}$, so the local address of node $MN_{0,40}$ at $Host_{40}$ is a 24 bit code which indicates this connection. For convenience, in FIGS. 6 and 7, the global address of a NAT is identified by the NAT name and the local address indicating a connection between a particular node $MN_X$ and a $Host_X$ is represented as $MN_X@Host_X$.

If a communication and/or data packet is to be sent from a node in one network to a node in another network, before data transfer can take place, a conventional NAT table is set up. By convention the node initiating contact is referred to as a corresponding node (CN). For node to node communication, the first set of actions is to establish a binding by the NATs for the networks to which the nodes are currently connected. The conventional process is described by the Internet Engineering Task Forces (IETF) Request for Comments (RFCs) 1631 and 3032. When a binding is established, an Internet Protocol (IP) data packet can be sent by the corresponding node (CN)

which traverses the global Internet and reaches NAT of the receiving node based on the binding established FIG. 7 illustrates the format of the conventional binding table established between the CN and the receiving node. The bindings are made up of the nodes' global and local address combinations. For example, node $MN_{0,A0}$ in network 10 as CN may communicate with node $MN_{0,B0}$ in network 50. For node $MN_{0,A0}$ the binding data is the combined Global Address NAT-A and the local address $MN_{0,A0}$@$Host_{A0}$. For node $MN_{0,B0}$, the binding data is the combined Global Address NAT-B and local address $MN_{0,B0}$@$Host_{B0}$.

The procedure for sending out a data packet from node $MN_{0,A0}$ to node $MN_{0,B0}$ is as follows. The packet is encoded with the global address NAT-A as the source address and the global address NAT-B as the destination address is sent from the source node $MN_{0,A0}$. The receiving NAT, NAT-B in this example, checks the binding in its table, and retrieves the local address of the receiving node's Host, $Host_{0B}$ in this example. The packet is then forwarded to that Host through which it is received by the node $MN_{0,B0}$. Where a node is not mobile, its binding data represents a permanent address to which any CN may send data under the conventional binding system and protocols. However, mobile nodes MN may change location so that simply addressing data to a prior known address does not assure delivery without some system to accommodate connection changes by the MN.

FIGS. 8 and 9 illustrate the architecture used to implement a micro-mobility protocol between the private networks shown. The architecture includes an entity called a Mobile-Home Database (MHD) associated with each NAT. This is a large directory, tightly coupled to each NAT, for keeping track of the MNs within the private network. It also indicates when the MN has moved to a foreign network (FN).

The MHD for each NAT preferably includes an index field for each mobile node, a home/away flag field indicating whether a mobile node is associated with the NAT, a local address or care of address (COA) field and a NAT address field. Each MN has a home Host in a home network which defines a Home Address (HA) which is analogous to the permanent local address of a non-mobile node in that it is the address that a CN will use to contact the MN. The default binding for an MN is a combination of the global address of the MN's home network's NAT and the MN's home address. If at home, the MN's default binding will be used to establish a NAT/NAT connection for the CN/MN communication.

All of the MNs whose home Host is associated with a particular NAT, i.e. the home network's NAT, have data records in that NAT's MHD. One convenient way to identify the mobile nodes is using their default or home address (HA), so the index field of a network's NAT's MHD preferably lists the HAs of all of the MNs whose home network is that network to identify the data record for each MN.

The flag field represents a logical field, preferably having a value 0 or a value 1 to represent a home or an away status with respect to the network. In the present example, 0 is used to indicate that the MN has a connection with a Host in the network and 1 is used to indicate that the MN has a connection with a different network. The local address field (COA) is used to indicate to which Host the MN is currently connected. Where the local address field entry is a Host associated with a foreign network, the global address field contains the global address of that foreign network's NAT. In such case the flag field is set to 1. When the flag field is 0, the global address value is not needed since the relevant global address is that of the MHD's NAT.

FIGS. 8 and 9 illustrate various example records for the MHDs of NAT-B and NAT-N of the networks 42 and 50, respectively, at a given point in time as illustrated in FIG. 6.

Where a MN is in communication with its home Host, as illustrated with respect to mobile nodes $MN_{0,B0}$, $MN_{0,B1}$ and $MN_{0,Nk}$, the associated flag field is set to 0 and the local or COA field entry is the same as the home address. No NAT address information is required.

For MNs which are associated with a Host which is not the MN's home Host, but is a Host in the MN's home network, the MHD of the MN's home network's NAT has data entries for the flag field as 0 and the local address (COA) as the current association of the MN with its non-home Host. For example, mobile node $MN_{1,B0}$ has a home host $Host_{B0}$, but is illustrated in FIG. 1 as connected to host $Host_{B1}$. The MN is identified in the index field by its HA, $MN_{1,B0}$@$Host_{B0}$, has 0 in the flag field and has $MN_{1,B0}$@$Host_{B1}$ as the COA as set forth in FIG. 8. The NAT address field information is not needed since the global address remains the same because $Host_{B1}$ and $Host_{B0}$ are associated with the same network with the associated global address, namely NAT-B.

Where a MN from one network connects with a host of a different network, the MN is registered in that network's NAT with a visiting address. For example, node $MN_{i,Nk}$ has as its home host $Host_{Nk}$ in network 50 which communicates with the Internet via NAT-N. In FIG. 6, node $MN_{i,Nk}$ is illustrated as visiting network 42 in connection with $Host_{B1}$ which is associated with NAT-B. Accordingly, mobile node $MN_{i,Nk}$ is assigned a visiting address VA represented as $MN_{i,Nk}$@$Host_{B1}$ in the MHD of NAT-B with a flag field 0 indicating its communication with the Internet through NAT-B and a local address of $MN_{i,Nk}$@$Host_{B1}$.

When the mobile node, such as $MN_{i,Nk}$, first initiates communication with the foreign network, for example, network 42, a communication is sent to the NAT of its home network, in this case, NAT-N, to enable efficient redirection of communications. The communication to the MN's home network's NAT changes the NAT's MHD data with respect to the listing for the MN by setting the flag field to 1 and providing binding data for further Internet communications. The binding data is comprised of the assigned visiting address VA and the global address of the NAT of the network which the MN is visiting.

For the example of mobile node $MN_{i,Nk}$ the MHD of NAT-N in FIG. 4 reflects a flag value of 1, a local address of $MN_{i,Nk}$@$Host_{B1}$ and a NAT address of NAT-B. A corresponding node attempting to communicate with mobile Node $MN_{i,Nk}$ will not be able to establish a binding with NAT-N since the flag in NAT-N's MHD is set to 1. In that case, the binding is established with the binding represented by the local address and NAT address fields for $MN_{i,Nk}$'s entry in NAT-N's MHD. Communication is then conducted establishing a binding with the foreign NAT, in the example NAT-B.

So long as the visiting MN does not establish an association with a Host of a different network, it will preferably retain its visiting address VA identification in the MHD of the NAT whose network it is visiting, which VA will be also reflected in the MHD of the mobile node's home network's NAT.

If the visiting mobile node establishes an association with another Host within the same network that it is visiting, it will retain its same VA identification in the MHD of the NAT which it is visiting, but will be provided with a new local address. That new local address will be stored in the visiting MN's MHD record's COA field and the visited network's NAT will direct communications to the MN based on that COA data. No change is required in the MN's home network's NAT's MHD in such case. For example, if $MN_{i,Nk}$ switches its association with Host$_{B1}$ and connects to Host$_{B0}$, the COA entry in the MHD of NAT-B will be changed from MN$_{i,Nk}$@Host$_{B1}$ to MN$_{i,Nk}$@Host$_{B0}$ and no change will be made in the entries in the MHD of NAT-N.

Preferably, the hosts will periodically determine whether a connection is still established with a visiting MN. If the visited host determines that the MN has disconnected and the MN has not established a connection with another host, the visited host can communicate this fact to its associated NAT which will change the COA for the visiting MN's entry to a null data state. An example of this is the entry for visiting node MN$_{h,Pq}$ in FIG. 8. That entry indicates that MN$_{h,Pq}$ had connected with foreign Host$_{B1}$, but is no longer connected to network 42. Thus, no connection of MN$_{h,Pq}$ is illustrated with any Host in FIG. 6. Such an entry will also indicate to a CN that the MN has not established a connection with another host, since the CN will only contact network 42 via the VA of MN$_{h,Pq}$, namely MN$_{h,Pq}$@Host$_{B1}$, if MN$_{h,Pq}$'s home network's NAT's MHD record has not been updated. If a CN attempts to communicate with the visiting node at that time and is referred to the visited network's NAT by the MN's home Host's NAT, a binding will not be established and the communication will fail.

When a MN's home network's NAT receives a communication to change the binding information for the MN from one foreign NAT to another, it preferably sends a message to the first foreign NAT reflecting that the MN is no longer visiting that NAT's network, so that the visiting node record can be deleted from the first foreign NAT's MHD. Such a message is preferably also sent, when a MN returns to its home network after visiting other networks.

The CN never needs to know the current location of the MN. The CN only needs to be aware of the static, default binding based on a MN's home address (HA) and home network's global address. This arrangement saves the flurry of registration messages from being sent over the global Internet.

The tight coupling of the MHDs to the NATs means that an IP data packet does not have to travel first to the home network. The packet can be tunneled directly to the foreign network where the MN is located. This avoids the infamous triangle routing problem.

The micro-mobility protocol for MNs roaming across multiple foreign networks (FNs) starts with the CN's NAT trying to establish a binding with the MN's home network's NAT. The process fails, when the status-bit in the MN's home network's NAT's MHD is a 1. This indicates that the MN is not currently in its home network (HN); it is in a FN. The FN has assigned a VA to the MN which is stored in the MN's home network's NAT's MHD along with the static global address of the FN. That binding data is sent back to the CN's NAT and the CN's NAT then establishes binding with the FN's NAT. The rest of the protocol then proceeds the same way as if the MN were connected with a host in its home network.

When during a communication with a CN, a MN moves from one foreign network FN$_1$ to a different network FN$_2$, the entries for the MN in the MHD of FN$_1$ are preferably set 0, NULL, NULL when the MN loses contact with the FN$_1$. When the MN then moves to the different FN$_2$, NAT-FN$_2$. The MN is assigned a VA of MN@Host$_2$, NULL. The binding data (MN@Host$_2$, NAT-FN$_2$) is sent to the MN's home network's NAT and the CN's NAT. A new binding is established between the CN's NAT and NAT-FN$_2$. The rest of the Protocol then proceeds as described above.

When during a communication with a CN, a MN moves from a foreign network FN$_1$ to back to its home network HN, the entry for the MN in the MHD of the NAT of FN$_1$ is preferably set 0, NULL, NULL when the MN loses contact with the FN$_1$. When the MN then moves to its HN, it communicates with its HN via a host, Host$_{HN}$, associated with its HN's NAT, NAT-HN. Note that Host$_{HN}$ may or may not be the MN's home host, Host$_{Home}$. In its HN's NAT's MHD, the MN already has a data record for its HA of MN@Host$_{Home}$. That record is preferably then changed to set the associated data fields to 0, MN@Host$_{HN}$, NULL. The binding data (MN@Host$_{Home}$, NAT-HN) is sent to the CN's NAT. A new binding is established between the CN's NAT and NAT-HN. The rest of the protocol then proceeds as described above.

The CN's NAT in the above cases would normally be the CN's home network's NAT. However, if the CN is a MN which is visiting a FN, the CN's NAT is the NAT of the FN being visited.

Other variations and alternatives will be recognized by those of ordinary skill in the art as within the scope of the invention are intended to be included herein.

What is claimed is:

1. A Network Address Translation router (NAT) for a network which identifies the NAT with a unique global address of the network and has at least one Host having a service area in which the host can communicate data to Mobile Nodes (MNs), each MN identified with a default binding comprising a local address of a home host within a home network and a global address of the home network, the NAT comprising:
   a Mobile-Home Database (MHD) configured to store current binding information for MNs in data records reflecting a local address, a global address and a home or an away indication;
   the MHD being configured to store such data records for MNs that have a current binding with a Host within the NAT's network that reflect the local address of the MN's current Host, the global address of the NAT's network and a home indication; and
   the MHD being configured to store such data records for MNs that have their home host's within the NAT's network and that have a current binding with a Host not within the NAT's network that reflect the local address of the MN's current Host, a global address of a network associated with the MN's current Host and an away indication.

2. The NAT according to claim 1 wherein the MHD records each comprise an MN identification field, a 24 bit local address field for storing local address information, a 24 bit global address field for storing global address information and a one bit location field.

3. The NAT according to claim 2 wherein the MHD is configured to store a null address in the 24 bit global address field of a data record to indicate the global address of the NAT's network, and a 1 or a 0 in the one bit location field of a data record as a home or an away indication.

4. An Access Router (AR) having a unique Internet Protocol (IP) address and a geographic access range in which the AR communicates data to Mobile Nodes (MNs), each MN is associated with a home AR, the AR comprising:
   a Node Location Table (NLT) configured to store current location information for MNs in data records reflecting an MN identification and an IP address of an AR;
   the NLT being configured to store such data records for MNs that have the AR as a home AR and that are in direct communication with the AR that reflects the MN's identification and the IP address of the AR;
   the NLT being configured to store such data records for MNs that have the AR as a home AR and that are in direct communication with a different AR that reflects the MN's identification and the IP address of the different AR whereby each MN that has the AR as a home AR is movable outside the access range of the AR to a location within the access range of another AR to receive data via the other AR by communicating to the AR the IP address of the other AR as its current location; and the AR being configured to respond to queries by corresponding node (CNs) for data communication with MNs that have the AR as a home AR and that are in direct communication with other ARs such that in response to a query from a CN for data communication with an MN that has the AR as a home AR and that is in direct communication with a different AR, the AR sends the CN the IP address of the different AR from the record identifying the MN in the NLT.

5. The AR according to claim 4 wherein the NLT records each comprise an MN identification field and an IP address field.

6. A wireless communication apparatus comprising the AR of claim 4.

7. The apparatus of claim 6 including a plurality of Access Points configured to provide wireless communication with Mobile Nodes.

8. The apparatus of claim 6 including an Access Network Gateway configured to provide communication with the Internet and an Access Point configured to provide wireless communication with Mobile Nodes.

9. A wireless communication apparatus comprising the NAT of claim 1.

10. The apparatus of claim 9 including a plurality of Hosts configured to provide wireless communication with Mobile Nodes.

* * * * *

UNITED STATES PATENT AND TRADEMARK OFFICE
CERTIFICATE OF CORRECTION

| | | |
|---|---|---|
| PATENT NO. | : 7,573,890 B2 | Page 1 of 2 |
| APPLICATION NO. | : 11/542842 | |
| DATED | : August 11, 2009 | |
| INVENTOR(S) | : Shahrier et al. | |

It is certified that error appears in the above-identified patent and that said Letters Patent is hereby corrected as shown below:

IN THE SPECIFICATION

At column 4, line 39, before the word "configured" insert --identified in the Host's network's MHD or the network's NAT can be--.

At column 4, line 40, after the word "nodes" insert --.--.

At column 5, line 16, after the word "Protocol" delete "(UPD)" and insert --(UDP)--.

At column, 6, line 7, after the word "to" delete "a" and insert --an--.

At column 6, line 12, after the word "overhead" delete "make" and insert --makes--.

At column 6, line 39, after the word "between" delete "a" and insert --an--.

At column 7, line 10, after the word "Point" delete "$AR_{1,0}$ and Access Router $AR_1$." and insert --$AP_{i,0}$ and Access Router $AR_i$.--.

At column 7, line 19, after the word "if" delete "a" and insert --an--.

At column 10, line 48, after the word "local" delete "address" and insert --addresses--.

At column 12, line 4, after the word "where" delete "a" and insert --an--.

At column 12, line 22, after the word "where" delete "a" and insert --an--.

At column, 13, line 24, after the word "where" delete "a" and insert --an--.

At column 13, line 30, before "MN" delete "a" and insert therefor --an--.

At column 13, line 34, before "MN's" delete "a" and insert therefor --an--.

At column 13, line 48, before "FN" delete "a" and insert therefor --an--.

At column 13, line 56, before "MN" delete "a" and insert therefor --an--.

At column 13, lines 60 & 61, after the words "different $FN_2$," delete "$NAT-FN_2$. The MN is assigned a VA of $MN@Host_2$, NULL." and insert therefor --it communicates with $FN_2$ via a host, $Host_2$, associated with the NAT of $FN_2$, Signed and Sealed this
Eleventh Day of October, 2011

David J. Kappos
*Director of the United States Patent and Trademark Office*

CERTIFICATE OF CORRECTION (continued)
U.S. Pat. No. 7,573,890 B2

NAT-FN$_2$. The MN is assigned a VA of MN@Host$_2$ such that the entries for that VA in the MHD of NAT-FN$_2$ are set to 0, MN@Host$_2$, NULL.--.

At column 13, line 66, before "MN" delete "a" and insert therefor --an--.

At column 14, line 14, before "MN" delete "a" and insert therefor --an--15.

At column 14, line 15, before "FN" delete "a" and insert therefor --an--.